United States Patent
Parsons et al.

(10) Patent No.: US 9,580,750 B2
(45) Date of Patent: Feb. 28, 2017

(54) PI3K PATHWAY MUTATIONS IN CANCER

(75) Inventors: Donald William Parsons, Ellicott City, MD (US); Tian-li Wang, Baltimore, MD (US); Yardena Samuels, Baltimore, MD (US); Alberto Bardelli, Turin (IT); Christopher Lengauer, Noisy-le-Roi (FR); Victor Velculescu, Dayton, MD (US); Kenneth W. Kinzler, Bel Air, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 2107 days.

(21) Appl. No.: 11/920,860

(22) PCT Filed: May 23, 2006

(86) PCT No.: PCT/US2006/019748
§ 371 (c)(1),
(2), (4) Date: Nov. 12, 2010

(87) PCT Pub. No.: WO2006/127607
PCT Pub. Date: Nov. 30, 2006

(65) Prior Publication Data
US 2011/0059434 A1    Mar. 10, 2011

Related U.S. Application Data

(60) Provisional application No. 60/683,738, filed on May 23, 2005.

(51) Int. Cl.
| | | |
|---|---|---|
| C12Q 1/62 | (2006.01) | |
| G01N 33/574 | (2006.01) | |
| C07K 16/40 | (2006.01) | |
| C12Q 1/68 | (2006.01) | |
| C12Q 1/48 | (2006.01) | |
| G01N 33/50 | (2006.01) | |

(52) U.S. Cl.
CPC ........... *C12Q 1/6883* (2013.01); *C12Q 1/485* (2013.01); *G01N 33/5044* (2013.01); *G01N 33/57419* (2013.01); *C12Q 2600/136* (2013.01); *C12Q 2600/156* (2013.01)

(58) Field of Classification Search
CPC .. A61K 2300/00; C12Q 1/6886; C12Q 1/485; C12Q 2600/106; C12Q 2600/158; C12Q 2600/112; C12Q 1/6883; C12Q 2600/118; C12Q 2600/156
See application file for complete search history.

(56) References Cited

U.S. PATENT DOCUMENTS

| | | |
|---|---|---|
| 2005/0019746 A1 | 1/2005 | Seeny |
| 2005/0032185 A1 | 2/2005 | Alessi |
| 2005/0216961 A1* | 9/2005 | Delaney .................. 800/10 |

OTHER PUBLICATIONS

Yuan et al (Oncogene, 2000, 19:2324-2330).*
Ruggeri et al (Molecular Carcinogenesis, 1998, 21:81-86).*
Roy et al (Carcinogenesis, 2002, 23:201-205).*
Bellacosa et al (Cancer Biology & Therapy, 2004, 3:268-275).*
A. Bardelli et al., "Mutational Analysis of the Tyrosine Kinome in Colorectal Cancers," Science (2003), 300, 949.
P. A. Futreal et al., "A Census of Human Cancer Genes," Nat. Rev. Cancer 4, (2004), pp. 177-183.
H. Davies et al., "Mutations of the BRAF Gene in Human Cancer," Nature (2002), 417, pp. 949-954.
D. W. Parsons et al., "Colorectal Cancer: Mutations in a Signalling Pathway," Nature, Aug. 11, 2005;436 (7052):792, (Abstract only).
A. D. Ramos et al., "Pharmacological Inhibitors of PI3K/Akt Potentiate the Apoptotic Action of the Antileukemic Drug Arsenic Trioxide via Glutathione Depletion and Increased Peroxide Accumulation in Myeloid Leukemia Cells," Blood, May 15, 2005, vol. 105, No. 10, pp. 4013-4020, (Abstract only).
A. M. Martelli et al., "A New Selective AKT Pharmacological Inhibitor Reduces Resistance to Chemotherapeutic Drugs, TRAIL, All-Trans-Retinoic Acid, and Ionizing Radiation of Human Leukemia Cells," Leukemia, Sep. 17, 2003(9):1794-805, (Abstract only).
D. Yang et al., "Structure-Based Discovery of Novel Inhibitors of Protein Kinase," Medicine, Anatomy and Physiology, Aug. 15, 2002-Aug. 14, 2003, (Abstract only).
P. Blume-Jensen et al., "Oncogenic Kinase Signaling," Nature, May 17, 2001, vol. 411, pp. 355-365.
Y. Samuels et al., "Mutant PIK3CA Promotes Cell Growth and Invasion of Human Cancer Cells," Cancer Cell, Jun. 2005, vol. 7, pp. 561-573.
P.A. Steck et al., "Identification of a Candidate Tumour Suppressor Genes, MMAC1, at Chromosome 10q23.3 that is Mutated in Multiple Advanced Cancers," Nat Genet. Apr. 1997;15(4):356-62, (Abstract only).
J. Li et al., "PTEN, a Putative Protein Tyrosine Phosphatase Gene Mutated in Human Brain, Breast, and Prostate Cancer," Science, Mar. 28, 1997: 275(5308):1876-8, (Abstract only).
P. Stephens et al., "A Screen of the Complete Protein Kinase Gene Family Identifies Diverse Patterns of Somatic Mutations in Human Breast Cancer," Nature Genetics, Jun. 2005, vol. 37, No. 6, pp. 590-592.

(Continued)

*Primary Examiner* — Julie Wu
(74) *Attorney, Agent, or Firm* — Banner & Witcoff, Ltd.

(57) ABSTRACT

Given the important role of protein kinases in pathways affecting cellular growth and invasion, we have analyzed 340 serine/threonine kinases for genetic mutations in colorectal cancers. Mutations in eight genes were identified, including three members of the phosphatidylinositol-3-kinase (PI3K) pathway; the alterations in the latter genes each occurred in different tumors and did not overlap with mutations in PIK3CA or other non-serine-threonine kinase (STK) members of the PI3K pathway, suggesting that mutations in any of these genes had equivalent tumorigenic effects. These data demonstrate that the PI3K pathway is a major target for mutational activation in colorectal cancers and provide new opportunities for therapeutic intervention.

13 Claims, 14 Drawing Sheets

(56) References Cited

OTHER PUBLICATIONS

S. Kang et al., "Phosphatidylinositol 3-Kinase Mutations Identified in Human Cancer Are Oncogneic," PNAS, Jan. 18, 2005, vol. 102, No. 3, pp. 802-807.
D. W. Parsons et al., "Colorectal Caner Mutations in a Signalling Pathway," Nature, Aug. 11, 2005, vol. 436, published online Aug. 10, 2005, p. 792 (Supplementary table 2).
PCT IPRP.

* cited by examiner

Fig. 2. Serine / threonine kinome genes analyzed

| Gene name | Kinome name | Kinome group | Genbank Accession | Celera accession |
|---|---|---|---|---|
| AKT1 | AKT1 | AGC | NM_005163 | hCT88042 |
| AKT2 | AKT2 | AGC | NM_001626 | hCT11881 |
| AKT3 | AKT3 | AGC | NM_005465 | hCT6401 |
| ADRBK1 | BARK1 | AGC | NM_001619 | hCT11218 |
| ADRBK2 | BARK2 | AGC | NM_005160 | hCT31349 |
| CIT | CRIK | AGC | NM_007174 | hCT18924 |
| DMPK | DMPK1 | AGC | NM_004409 | hCT1964464 |
| HSMDPKIN | DMPK2 | AGC | XM_045615 | hCT1814288 |
| GPRK2L | GPRK4 | AGC | NM_005307 | hCT1970766 |
| GPRK5 | GPRK5 | AGC | NM_005308 | hCT1951814 |
| GPRK6 | GPRK6 | AGC | NM_002082 | hCT31538 |
| GPRK7 | GPRK7 | AGC | NM_017572 | hCT7580 |
| LATS1 | LATS1 | AGC | NM_004690 | hCT1953584 |
| LATS2 | LATS2 | AGC | NM_014572 | hCT1812979 |
| SAST | MAST1 | AGC | XM_032034 | hCT173001 |
| MAST205 | MAST2 | AGC | NM_015112 | hCT13189 |
| KIAA0561 | MAST3 | AGC | XM_038150 | hCT28114 |
| KIAA0303 | MAST4 | AGC | XM_291141 | hCT1950015 |
| FLJ14813 | MASTL | AGC | NM_032844 | hCT16367 |
| CDC42BPA | MRCKa | AGC | NM_003607 | hCT1776117 |
| CDC42BPB | MRCKb | AGC | NM_006035 | hCT15866 |
| RPS6KA5 | MSK1 | AGC | NM_004755 | hCT1952342 |
| RPS6KA4 | MSK2 | AGC | NM_003942 | hCT14489 |
| NDR | NDR1 | AGC | NM_007271 | hCT5820 |
| STK38L | NDR2 | AGC | NM_015000 | hCT30012 |
| RPS6KB1 | p70S6K | AGC | NM_003161 | hCT1815775 |
| RPS6KB2 | p70S6Kb | AGC | NM_003952 | hCT12140 |
| PDPK1 | PDK1 | AGC | NM_002613 | hCT6648 |
| PRKACA | PKACa | AGC | NM_002730 | hCT18662 |
| PRKACB | PKACb | AGC | NM_002731 | hCT14767 |
| PRKACG | PKACg | AGC | NM_002732 | hCT2259211 |
| PRKCA | PKCa | AGC | NM_002737 | hCT20429 |
| PRKCB1 | PKCb | AGC | NM_002738 | hCT1950274 |
| PRKCD | PKCd | AGC | NM_006254 | hCT8601 |
| PRKCE | PKCe | AGC | NM_005400 | hCT6798 |
| PRKCG | PKCg | AGC | NM_002739 | hCT12033 |
| PRKCH | PKCh | AGC | NM_006255 | hCT13455 |
| PRKCI | PKCi | AGC | NM_002740 | hCT9296 |
| PRKCQ | PKCt | AGC | NM_006257 | hCT1967788 |
| PRKCZ | PKCz | AGC | NM_002744 | hCT15713 |

FIG. 2

| | | | | |
|---|---|---|---|---|
| PRKG1 | PKG1 | AGC | NM_006258 | hCT1950046 |
| PRKG2 | PKG2 | AGC | NM_006259 | hCT16201 |
| PRKCL1 | PKN1 | AGC | NM_002741 | hCT18657 |
| PRKCL2 | PKN2 | AGC | NM_006256 | hCT14845 |
| PKN3 | PKN3 | AGC | NM_013355 | hCT87421 |
| PRKX | PRKX | AGC | NM_005044 | hCT9547 |
| PRKY | PRKY | AGC | NM_002760 | hCT1950016 |
| RHOK | RHOK | AGC | NM_002929 | hCT9702 |
| ROCK1 | ROCK1 | AGC | NM_005406 | hCT29270 |
| | | | | hCT1820109 |
| ROCK2 | ROCK2 | AGC | NM_004850 | hCT12724 |
| RPS6KA2 | RSK1 | AGC | NM_021135 | hCT6040 |
| RPS6KA3 | RSK2 | AGC | NM_004586 | hCT9007 |
| RPS6KA1 | RSK3 | AGC | NM_002953 | hCT10675 |
| RPS6KA6 | RSK4 | AGC | NM_014496 | hCT8801 |
| RPS6KC1 | RSKL1 | AGC | NM_012424 | hCT30691 |
| RPS6KL1 | RSKL2 | AGC | NM_031464 | hCT13451 |
| SGK | SGK | AGC | NM_005627 | hCT23928 |
| SGK2 | SGK2 | AGC | NM_016276 | hCT28381 |
| SGKL | SGK3 | AGC | NM_013257 | hCT9448 |
| FLJ25006 | SgK494 | AGC | NM_144610 | hCT22988 |
| MGC22688 | YANK1 | AGC | NM_145001 | hCT28738 |
| HSA250839 | YANK2 | AGC | NM_018401 | hCT1953081 |
| PKE | YANK3 | AGC | NM_173575 | hCT14748 |
| | | | | hCT1767488 |
| PRKAA1 | AMPKa1 | CAMK | NM_006251 | hCT28571 |
| PRKAA2 | AMPKa2 | CAMK | NM_006252 | hCT13256 |
| KIAA1811 | BRSK1 | CAMK | NM_032430 | hCT29475 |
| | | | | hCT1770914 |
| STK29 | BRSK2 | CAMK | NM_003957 | hCT1817087 |
| CAMK1 | CaMK1a | CAMK | NM_003656 | hCT12640 |
| LOC139728 | CaMK1b | CAMK | XM_060051 | hCT30475 |
| CKLiK | CaMK1d | CAMK | NM_020397 | hCT1951838 |
| CAMK1G | CaMK1g | CAMK | NM_020439 | hCT14094 |
| CAMK2A | CaMK2a | CAMK | NM_015981 | hCT29857 |
| CAMK2B | CaMK2b | CAMK | NM_001220 | hCT9356 |
| CAMK2D | CaMK2d | CAMK | NM_001221 | hCT1952248 |
| CAMK2G | CaMK2g | CAMK | XM_044349 | hCT11620 |
| CaMK4 | CaMK4 | CAMK | NM_001744 | hCT28678 |
| LOC91807 | caMLCK | CAMK | NM_182493 | hCT14427 |
| CASK | CASK | CAMK | NM_003688 | hCT1951807 |
| CHEK1 | CHK1 | CAMK | NM_001274 | hCT30161 |
| CHEK2 | CHK2 | CAMK | NM_007194 | hCT32245 |
| DAPK1 | DAPK1 | CAMK | NM_004938 | hCT18877 |

FIG. 2 (continued)

| | | | | |
|---|---|---|---|---|
| DAPK2 | DAPK2 | CAMK | NM_014326 | hCT21851 |
| | | | | hCT23580 |
| DAPK3 | DAPK3 | CAMK | NM_001348 | hCT14628 |
| DCAMKL1 | DCAMKL1 | CAMK | NM_004734 | hCT23387 |
| MGC45428 | DCAMKL2 | CAMK | NM_152619 | hCT9098 |
| KIAA1765 | DCAMKL3 | CAMK | XM_047355 | hCT7736 |
| STK17A | DRAK1 | CAMK | NM_004760 | hCT10495 |
| STK17B | DRAK2 | CAMK | NM_004226 | hCT11150 |
| HUNK | HUNK | CAMK | NM_014586 | hCT401149 |
| STK11 | LKB1 | CAMK | NM_000455 | hCT12664 |
| MAPKAPK2 | MAPKAPK2 | CAMK | NM_004759 | hCT13298 |
| MAPKAPK3 | MAPKAPK3 | CAMK | NM_004635 | hCT1951041 |
| MAPKAPK5 | MAPKAPK5 | CAMK | NM_003668 | hCT31402 |
| MARK1 | MARK1 | CAMK | NM_018650 | hCT16244 |
| MARK2 | MARK2 | CAMK | NM_004954 | hCT1950044 |
| MARK3 | MARK3 | CAMK | NM_002376 | hCT16625 |
| MARK4 | MARK4 | CAMK | NM_031417 | hCT13235 |
| MELK | MELK | CAMK | NM_014791 | hCT22552 |
| MKNK1 | MNK1 | CAMK | NM_003684 | hCT1967057 |
| MKNK2 | MNK2 | CAMK | NM_017572 | hCT13815 |
| MGC42105 | NIM1 | CAMK | NM_153361 | hCT28035 |
| ARK5 | NuaK1 | CAMK | NM_014840 | hCT7133 |
| SNARK | NuaK2 | CAMK | NM_030952 | hCT6013 |
| KIAA1639 | Obscn | CAMK | XM_290923 | hCT53947 |
| PASK | PASK | CAMK | NM_015148 | hCT1958412 |
| PHKg1 | PHKg1 | CAMK | NM_006213 | hCT1952970 |
| PHKg2 | PHKg2 | CAMK | NM_000294 | hCT12239 |
| PIM1 | PIM1 | CAMK | NM_002648 | hCT24413 |
| PIM2 | PIM2 | CAMK | NM_006875 | hCT10898 |
| PIM3 | PIM3 | CAMK | NM_001001852 | hCT87711 |
| PRKCM | PKD1 | CAMK | NM_002742 | hCT1956115 |
| PKD2 | PKD2 | CAMK | NM_000297 | hCT12178 |
| PRKCN | PKD3 | CAMK | NM_005813 | hCT7941 |
| CTRL | PSKH1 | CAMK | NM_001907 | hCT19257 |
| PSKH2 | PSKH2 | CAMK | NM_033126 | hCT1651265 |
| KIAA0781 | QIK | CAMK | XM_041314 | hCT30715 |
| KIAA0999 | QSK | CAMK | NM_025164 | hCT32605 |
| LOC340156 | SgK085 | CAMK | XM_291158 | hCT13977 |
| MGC4796 | SgK495 | CAMK | XM_029031 | hCT1826784 |
| SNF1LK | SIK | CAMK | NM_173354 | hCT401299 |
| MYLK2 | skMLCK | CAMK | NM_033118 | hCT30068 |
| MYLK | smMLCK | CAMK | NM_005965 | hCT1955467 |
| SNRK | SNRK | CAMK | NM_017719 | hCT17934 |
| APEG1 | SPEG | CAMK | NM_005876 | hCT1955090 |

FIG. 2 (continued)

| | | | | |
|---|---|---|---|---|
| SSTK | SSTK | CAMK | NM_032037 | hCT1640514 |
| STK33 | STK33 | CAMK | NM_030906 | hCT15008 |
| Trad | Trad | CAMK | NM_007064 | hCT1958122 |
| C8FW | Trb1 | CAMK | NM_025195 | hCT6949 |
| Trb2 | Trb2 | CAMK | NM_021643 | hCT6932 |
| C20orf97 | Trb3 | CAMK | NM_021158 | hCT31129 |
| Trio | Trio | CAMK | NM_007118 | hCT28221 |
| STK22D | TSSK1 | CAMK | NM_032028 | hCT1642687 |
| STK22B | TSSK2 | CAMK | NM_053006 | hCT1641214 |
| STK22C | TSSK3 | CAMK | NM_052841 | hCT32883 |
| C14orf20 | TSSK4 | CAMK | NM_174944 | hCT31443 |
| TTN | TTN | CAMK | NM_003319 | hCT2294313 |
| MGC8407 | VACAMKL | CAMK | NM_024046 | hCT1962107 |
| CSNK1A1 | CK1a | CK1 | NM_001892 | hCT1962993 |
| MGC33182 | CK1a2 | CK1 | NM_145203 | hCT24004 |
| CSNK1D | CK1d | CK1 | NM_001893 | hCT9868 |
| CSNK1E | CK1e | CK1 | NM_001894 | hCT32966 |
| CSNK1G1 | CK1g1 | CK1 | NM_022048 | hCT1966427 |
| CSNK1G2 | CK1g2 | CK1 | NM_001319 | hCT13814 |
| CSNK1G3 | CK1g3 | CK1 | NM_004384 | hCT1961334 |
| TTBK1 | TTBK1 | CK1 | XM_166453 | hCT1645996 |
| TTBK2 | TTBK2 | CK1 | NM_173500 | hCT31688 |
| VRK1 | VRK1 | CK1 | NM_003384 | hCT15630 |
| VRK2 | VRK2 | CK1 | NM_006296 | hCT6222 |
| VRK3 | VRK3 | CK1 | NM_016440 | hCT12192 |
| CCRK | CCRK | CMGC | NM_012119 | hCT1781925 |
| CDC2 | CDC2 | CMGC | NM_001786 | hCT31496 |
| CDK10 | CDK10 | CMGC | NM_003674 | hCT1953801 |
| CDK11 | CDK11 | CMGC | NM_015076 | hCT25091 |
| CDK2 | CDK2 | CMGC | NM_001798 | hCT16113 |
| CDK3 | CDK3 | CMGC | NM_001258 | hCT32152 |
| CDK4 | CDK4 | CMGC | NM_000075 | hCT31395 |
| CDK5 | CDK5 | CMGC | NM_004935 | hCT9752 |
| CDK6 | CDK6 | CMGC | NM_001259 | hCT9752 |
| CDK7 | CDK7 | CMGC | NM_001799 | hCT1963046 |
| CDK8 | CDK8 | CMGC | NM_001260 | hCT1957890 |
| CDK9 | CDK9 | CMGC | NM_001261 | hCT9609 |
| CDKL1 | CDKL1 | CMGC | NM_004196 | hCT13120 |
| CDKL2 | CDKL2 | CMGC | NM_003948 | hCT15503 |
| CDKL3 | CDKL3 | CMGC | NM_016508 | hCT1784151 |
| LOC344387 | CDKL4 | CMGC | NM_003948 | hCT6759 |
| CDKL5 | CDKL5 | CMGC | NM_003159 | hCT1767745 |
| CDC2L5 | CHED | CMGC | NM_003718 | hCT8314 |
| | | | | hCT1817396 |

FIG. 2 (continued)

| | | | | |
|---|---|---|---|---|
| CLK1 | CLK1 | CMGC | NM_004071 | hCT1967294 |
| CLK2 | CLK2 | CMGC | NM_001291 | hCT7150 |
| CLK3 | CLK3 | CMGC | NM_001292 | hCT1785808 |
| | | | | hCT1952452 |
| CLK4 | CLK4 | CMGC | NM_020666 | hCT11173 |
| CRK7 | CRK7 | CMGC | NM_016507 | hCT1815615 |
| DYRK1A | DYRK1A | CMGC | NM_001396 | hCT2296218 |
| DYRK1B | DYRK1B | CMGC | NM_004714 | hCT2276788 |
| DYRK2 | DYRK2 | CMGC | NM_003583 | hCT1812670 |
| DYRK3 | DYRK3 | CMGC | NM_003582 | hCT1962300 |
| DYRK4 | DYRK4 | CMGC | NM_003845 | hCT16080 |
| MAPK3 | Erk1 | CMGC | XM_055766 | hCT1809250 |
| MAPK1 | Erk2 | CMGC | NM_002745 | hCT1953846 |
| MAPK6 | Erk3 | CMGC | NM_002748 | hCT1825881 |
| MAPK4 | Erk4 | CMGC | NM_002747 | hCT14799 |
| MAPK7 | Erk5 | CMGC | NM_002749 | hCT21851 |
| ERK8 | Erk7 | CMGC | NM_139021 | hCT22884 |
| GSK3A | GSK3A | CMGC | NM_019884 | hCT12988 |
| GSK3B | GSK3B | CMGC | NM_002093 | hCT1960900 |
| HIPK1 | HIPK1 | CMGC | NM_152696 | hCT29887 |
| HIPK2 | HIPK2 | CMGC | NM_014075 | hCT1951429 |
| HIPK3 | HIPK3 | CMGC | NM_005734 | hCT18709 |
| FLJ32818 | HIPK4 | CMGC | NM_144685 | hCT11878 |
| ICK | ICK | CMGC | NM_014920 | hCT11897 |
| MAPK8 | JNK1 | CMGC | NM_002750 | hCT14846 |
| MAPK9 | JNK2 | CMGC | NM_002752 | hCT6303 |
| MAPK10 | JNK3 | CMGC | NM_002753 | hCT6118 |
| MAK | MAK | CMGC | NM_005906 | hCT28402 |
| RAGE | MOK | CMGC | NM_014226 | hCT13986 |
| STK23 | MSSK1 | CMGC | NM_014370 | hCT30469 |
| NLK | NLK | CMGC | NM_016231 | hCT22985 |
| MAPK14 | p38a | CMGC | NM_001315 | hCT1960854 |
| MAPK11 | p38b | CMGC | NM_002751 | hCT2264480 |
| MAPK13 | p38d | CMGC | NM_002754 | hCT6803 |
| MAPK12 | p38g | CMGC | NM_002969 | hCT1961565 |
| PCTK1 | PCTAIRE1 | CMGC | NM_006201 | hCT1953016 |
| PCTK2 | PCTAIRE2 | CMGC | NM_002595 | hCT24315 |
| PCTK3 | PCTAIRE3 | CMGC | XM_053746 | hCT6018 |
| PFTK1 | PFTAIRE1 | CMGC | NM_012395 | hCT1960141 |
| ALS2CR7 | PFTAIRE2 | CMGC | NM_139158 | hCT8032 |
| CDC2L1 | PITSLRE | CMGC | NM_001787 | hCT201160 |
| PRPF4B | PRP4 | CMGC | NM_003913 | hCT13049 |
| SRPK1 | SRPK1 | CMGC | NM_003137 | hCT1965608 |
| SRPK2 | SRPK2 | CMGC | NM_003138 | hCT8054 |

FIG. 2 (continued)

| | | | | |
|---|---|---|---|---|
| AAK1 | AAK1 | Other | NM_014911 | hCT1815718 |
| AURKA | AurA | Other | NM_003600 | hCT1953375 |
| AURKB | AurB | Other | NM_004217 | hCT1962134 |
| AURKC | AurC | Other | NM_003160 | hCT83273 |
| BMP2K | BIKE | Other | NM_017593 | hCT14090 |
| BUB1 | BUB1 | Other | NM_004336 | hCT7859 |
| BUB1B | BUBR1 | Other | NM_001211 | hCT30203 |
| CaMKK1 | CaMKK1 | Other | NM_032294 | hCT24404 |
| CaMKK2 | CaMKK2 | Other | NM_006549 | hCT18503 |
| CDC7 | CDC7 | Other | NM_003503 | hCT14329 |
| CSNK2A1 | CK2a1 | Other | NM_001895 | hCT1963007 |
| | | | | hCT13077 |
| CSNK2A2 | CK2a2 | Other | NM_001896 | hCT7524 |
| STK35 | CLIK1 | Other | NM_080836 | hCT30873 |
| LOC149420 | CLIK1L | Other | NM_152835 | hCT1643508 |
| STK36 | Fused | Other | NM_015690 | hCT7341 |
| GAK | GAK | Other | NM_005255 | hCT25648 |
| EIF2AK4 | GCN2 | Other | XM_031612 | hCT29941 |
| GSG2 | Haspin | Other | NM_031965 | hCT1640001 |
| HRI | HRI | Other | NM_014413 | hCT6997 |
| CHUK | IKKa | Other | NM_001278 | hCT10488 |
| IKBKB | IKKb | Other | XM_032491 | hCT8445 |
| IKBKE | IKKe | Other | NM_014002 | hCT28260 |
| ERN1 | IRE1 | Other | NM_001433 | hCT31791 |
| ERN2 | IRE2 | Other | NM_033266 | hCT14229 |
| KIS | KIS | Other | NM_144624 | hCT6882 |
| MOS | MOS | Other | NM_005372 | hCT1646311 |
| STK16 | MPSK1 | Other | NM_003691 | hCT1955093 |
| PKMYT1 | MYT1 | Other | NM_004203 | hCT6639 |
| NEK1 | NEK1 | Other | XM_048605 | hCT1782240 |
| NEK10 | NEK10 | Other | XM_067518 | hCT1647764 |
| | | | | hCT1816037 |
| NEK11 | NEK11 | Other | NM_024800 | hCT1960408 |
| NEK2 | NEK2 | Other | NM_002497 | hCT14581 |
| NEK3 | NEK3 | Other | XM_045087 | hCT20280 |
| NEK4 | NEK4 | Other | NM_003157 | hCT8603 |
| LOC341676 | NEK5 | Other | XM_292160 | hCT1833667 |
| NEK6 | NEK6 | Other | NM_014397 | hCT1961411 |
| NEK7 | NEK7 | Other | NM_133494 | hCT32030 |
| NEK8 | NEK8 | Other | NM_178170 | hCT23002 |
| NEK9 | NEK9 | Other | NM_033116 | hCT13450 |
| NRBP | NRBP1 | Other | NM_013392 | hCT11844 |
| LOC340371 | NRBP2 | Other | NM_178564 | hCT31978 |
| TOPK | PBK | Other | NM_018492 | hCT8338 |

FIG. 2 (continued)

| | | | | |
|---|---|---|---|---|
| EIF2AK3 | PEK | Other | NM_004836 | hCT1788243 |
| PIK3R4 | PIK3R4 | Other | XM_030812 | hCT6820 |
| PINK1 | PINK1 | Other | NM_032409 | hCT30119 |
| PKR | PKR | Other | NM_002759 | hCT7942 |
| PLK | PLK1 | Other | NM_005030 | hCT14966 |
| SNK | PLK2 | Other | NM_006622 | hCT30836 |
| CNK | PLK3 | Other | NM_004073 | hCT9662 |
| STK18 | PLK4 | Other | NM_014264 | hCT28950 |
| C20orf64 | PRPK | Other | NM_033550 | hCT31275 |
| RNASEL | RNAseL | Other | NM_021133 | hCT15509 |
| LOC388228 | SBK | Other | XM_370948 | hCT6694 |
| SCYL1 | SCYL1 | Other | NM_020680 | hCT1785428 |
| FLJ10074 | SCYL2 | Other | NM_017988 | hCT12893 |
| PACE-1 | SCYL3 | Other | NM_020423 | hCT29250 |
| LOC284299 | SgK069 | Other | XM_210370 | hCT1951831 |
| MGC43306 | SgK071 | Other | XM_291304 | hCT19302 |
| LOC284299 | SgK110 | Other | XM_210370 | hCT1951830 |
| FLJ23356 | SgK196 | Other | NM_032237 | hCT1641972 |
| DKFZp761P0423 | SgK223 | Other | XM_291277 | hCT1774383 |
| KIAA2002 | SgK269 | Other | NM_024776 | hCT1647192 |
| TEX14 | SgK307 | Other | NM_031272 | hCT2287920 |
| STK31 | SgK396 | Other | NM_031414 | hCT1968194 |
| LOC342888 | SgK424 | Other | XM_292738 | hCT1814175 |
| LOC91461 | SgK493 | Other | XM_038576 | hCT6993 |
| KIAA0472 | SgK496 | Other | XM_290898 | hCT2324518 |
| PXK | Slob | Other | NM_017771 | hCT18875 |
| MGC16169 | TBCK | Other | NM_033115 | hCT1967078 |
| TBK1 | TBK1 | Other | NM_013254 | hCT31928 |
| TLK1 | TLK1 | Other | NM_012290 | hCT1961463 |
| TLK2 | TLK2 | Other | NM_006852 | hCT1959927 |
| | | | | hCT1813983 |
| TTK | TTK | Other | NM_003318 | hCT401209 |
| ULK1 | ULK1 | Other | NM_003565 | hCT1782676 |
| ULK2 | ULK2 | Other | NM_014683 | hCT21864 |
| DKFZP434C131 | ULK3 | Other | XM_044630 | hCT32081 |
| FLJ20574 | ULK4 | Other | NM_017886 | hCT18956 |
| Wee1 | Wee1 | Other | NM_003390 | hCT15100 |
| | Wee1B | Other | | hCT30704 |
| PRKWNK1 | Wnk1 | Other | NM_018979 | hCT1640957 |
| PRKWNK2 | Wnk2 | Other | NM_006648 | hCT1823545 |
| PRKWNK3 | Wnk3 | Other | NM_020922 | hCT1786956 |
| PRKWNK4 | Wnk4 | Other | NM_032387 | hCT1816276 |

FIG. 2 (continued)

| | | | | |
|---|---|---|---|---|
| MAP3K8 | COT | STE | NM_005204 | hCT30302 |
| MAP4K2 | GCK | STE | NM_004579 | hCT14486 |
| MAP4K1 | HPK1 | STE | NM_007181 | hCT1967684 |
| MAP4K5 | KHS1 | STE | NM_006575 | hCT13114 |
| MAP4K3 | KHS2 | STE | NM_003618 | hCT1950486 |
| STK10 | LOK | STE | NM_005990 | hCT32021 |
| MAP2K1 | MAP2K1 | STE | NM_002755 | hCT15627 |
| MAP2K2 | MAP2K2 | STE | NM_030662 | hCT14651 |
| MAP2K3 | MAP2K3 | STE | NM_002756 | hCT19523 |
| MAP2K4 | MAP2K4 | STE | NM_003010 | hCT1962180 |
| MAP2K5 | MAP2K5 | STE | NM_002757 | hCT1955465 |
| MAP2K6 | MAP2K6 | STE | NM_002758 | hCT1954134 |
| MAP2K7 | MAP2K7 | STE | NM_005043 | hCT1951272 |
| MAP3K1 | MAP3K1 | STE | XM_042066 | hCT31875 |
| MAP3K2 | MAP3K2 | STE | NM_006609 | hCT33890 |
| MAP3K3 | MAP3K3 | STE | NM_002401 | hCT33098 |
| MAP3K4 | MAP3K4 | STE | NM_005922 | hCT1950009 |
| MAP3K5 | MAP3K5 | STE | NM_005923 | hCT24551 |
| MAP3K6 | MAP3K6 | STE | NM_004672 | hCT10368 |
| MAP3K7 | MAP3K7 | STE | NM_003188 | hCT1950026 |
| FLJ23074 | MAP3K8 | STE | NM_025052 | hCT16784 |
| STK4 | MST1 | STE | NM_006282 | hCT29601 |
| STK3 | MST2 | STE | NM_006281 | hCT1952595 |
| STK24 | MST3 | STE | NM_003576 | hCT1962325 |
| MST4 | MST4 | STE | NM_016542 | hCT1961474 |
| MYO3A | MYO3A | STE | NM_017433 | hCT15737 |
| MYO3B | MYO3B | STE | NM_138995 | hCT1951804 |
| MAP3K14 | NIK | STE | NM_003954 | hCT18748 |
| OSR1 | OSR1 | STE | NM_005109 | hCT33706 |
| PAK1 | PAK1 | STE | NM_002576 | hCT1954872 |
| PAK2 | PAK2 | STE | NM_002577 | hCT1950976 |
| PAK3 | PAK3 | STE | NM_002578 | hCT8535 |
| PAK4 | PAK4 | STE | NM_005884 | hCT1957471 |
| PAK7 | PAK5 | STE | NM_020341 | hCT30866 |
| PAK6 | PAK6 | STE | NM_020168 | hCT30204 |
| SLK | SLK | STE | NM_014720 | hCT12938 |
| STK39 | STLK3 | STE | NM_013233 | hCT6851 |
| LYK5 | STLK5 | STE | NM_153335 | hCT1966006 |
| ALS2CR2 | STLK6 | STE | NM_018571 | hCT1967342 |
| KIAA1361 | TAO1 | STE | XM_290796 | hCT1819297 hCT1950048 hCT1783295 |
| TAO1 | TAO2 | STE | NM_004783 | hCT1828589 hCT1956039 |

FIG. 2 (continued)

| | | | | |
|---|---|---|---|---|
| JIK | TAO3 | STE | NM_016281 | hCT1815220 |
| STK25 | YSK1 | STE | NM_006374 | hCT24239 |
| MAP4K4 | ZC1/HGK | STE | NM_004834 | hCT1640566 |
| KIAA0551 | ZC2/TNIK | STE | XM_039796 | hCT1953098 |
| MINK | ZC3/MINK | STE | NM_015716 | hCT23877 |
| NRK | ZC4/NRK | STE | NM_198465 | hCT1950047 |

* For each STK the following are indicated: gene name, Genbank and Celera accessions, and kinome name and group. The kinome groups include A/G/C protein kinases (AGC), calcium/calmodulin-dependent protein kinases (CAMK), casein kinases (CK), CMGC kinases, homologs of yeast sterile 7/11/20 kinases (STE), and other kinases. In case of alternative splice forms, multiple Celera accession numbers are indicated.

FIG. 2 (continued)

Fig. 3. Mutations in the serine/threonine kinome in colorectal cancer

| Gene Name | Alternate Name | Celera Accession | Genbank Accession | Number of Mutations | Tumors | Nucleotide | Amino Acid | Domain | Evolutionary conservation |
|---|---|---|---|---|---|---|---|---|---|
| MAP2K4 | MKK4, JNKK1 | hCT1962180 | NM_003010 | 6 | HX168 | G401A | R134Q | kinase | c,m,r,d,a,ce |
| | | | | | HX31 | splice site | | kinase | |
| | | | | | MX17* | T774C | I258I | kinase | |
| | | | | | HX79 | G961A | V321M | kinase | c,m,r,d,ce |
| | | | | | HX73* | C977T | P326L | kinase | c,m,r,d,ce |
| | | | | | HX144 | G1292A | 3' UTR | | |
| MYLK2 | MLCK | hCT30068 | NM_033118 | 6 | MX17* | C5A | A2E | | r |
| | | | | | CX10* | G215A | S72N | | c,m,r |
| | | | | | MX23* | G356A | G119D | | m,r |
| | | | | | HX73* | G1019A | R340H | kinase | c,m,r |
| | | | | | CX27 | G1093A | G365R | kinase | c,m,r |
| | | | | | HX69* | C1626A | N542K | | c,m,r |
| PDPK1 | PDK1 | hCT6648 | NM_002613 | 3 | CX3 | C1061T | T354M | kinase | c,m,r,d |
| | | | | | CX10* | C1061T | T354M | kinase | c,m,r,d |
| | | | | | MX20 | C1581G | D527E | PH | c,m,r,d |
| PAK4 | | hCT1957471 | NM_005884 | 2 | CO86* | G835A | A279T | kinase | m,r |
| | | | | | HX63 | G985A | E329K | kinase | m,r |
| AKT2 | PKB BETA | hCT11881 | NM_001626 | 2 | Cx7* | A1107G | S302G | kinase | c,m,r,a |
| | | | | | Hx66* | G1315A | R371H | kinase | c,m,r |
| MARK3 | ETK-1 | hCT16625 | NM_002376 | 2 | MX24 | G518A | R173Q | kinase | c,m,r,d,a,ce |
| | | | | | HX60* | 691insG | frameshift | kinase | |
| PDIK1L | CLIK1L | hCT1643508 | NM_152835 | 1 | CX3 | A863G | K288R | kinase | c,m,r |
| CDC7 | | hCT14329 | NM_003503 | 1 | MX1 | C628A | L210I | kinase | c,m,r |

The number of somatic mutations observed among 204 colorectal cancers is indicated. The asterisks denote tumors that are mismatch repair deficient. Domain refers to the protein domain containing the indicated mutation (kinase domain or plextrin homology domain). Evolutionary conservation refers to the species in which an identical residue was observed in the homolog (c, chimp; m, mouse; r, rat; d, fly; a, mosquito; ce, worm). The splice site alteration in MAP2K4 was in position 5 of the donor site of exon 6.

Fig. 4. PI3K pathway genes analyzed

| Gene name | Alternate name | Genbank accession | Celera accession | Example 4 References |
|---|---|---|---|---|
| AKT1 | PKB | NM_005163 | hCT88042 | 5 |
| AKT2 | PKBβ | NM_001626 | hCT11881 | 5 |
| AKT3 | PKBγ | NM_005465 | hCT6401 | 5 |
| PDPK1 | PDK1 | NM_002613 | hCT6648 | 5 |
| IRS1 | HIRS-1 | NM_005544 | hCT9420 | 5 |
| IRS2 | | NM_003749 | hCT2302543 | 5 |
| PAK4 | | NM_005884 | hCT1957471 | 6 |
| PTEN | MMAC1 | NM_000314 | hCT14442 | 5, 7, 8 |
| PIK3CA | p110α | NM_006218 | hCT1640694 | 5, 9 |
| PIK3R1 | p85α | NM_181504 | hCT28562 | 5, 10 |
| PIK3R2 | p85β | NM_005027 | hCT2284491 | 5 |
| PIK3R3 | p55γ | NM_003629 | hCT2333952 | 5 |
| INSRR | IRR | NM_014215 | hCT31077 | 2, 11 |
| ERBB4 | HER4 | NM_005228 | hCT6470 | 2, 12 |

Fig. 5. Mutations of PI3K pathway genes in colorectal cancer

| Tumors | PDK1 | AKT2 | PAK4 | AKT2 / PAK4 amp | IRS2 amp | INSRR | ERBB4 | PTEN | PIK3CA |
|---|---|---|---|---|---|---|---|---|---|
| CX3# | T354M | wt | wt | wt | wt | wt | wt | wt | wt |
| CX10* | T354M | wt | wt | wt | wt | wt | wt | wt | wt |
| MX20# | D527E | wt | wt | wt | wt | wt | wt | wt | wt |
| CX7* | wt | S302G | wt | wt | wt | wt | wt | wt | wt |
| HX66* | wt | R371H | wt | wt | wt | wt | wt | wt | wt |
| CO86*# | wt | wt | A279T | wt | wt | wt | wt | 800del / 968del | wt |
| HX63 | wt | wt | E329K | wt | wt | wt | wt | wt | wt |
| CO78 | wt | wt | wt | 15 fold | wt | wt | wt | wt | wt |
| CO82 | wt | wt | wt | 8 fold | wt | wt | wt | wt | wt |
| CO84 | wt | wt | wt | wt | 12 fold | wt | wt | wt | wt |
| CO69 | wt | wt | wt | wt | 7 fold | wt | wt | wt | wt |
| HX160# | wt | wt | wt | wt | 6 fold | wt | wt | wt | wt |
| MX5# | wt | wt | wt | wt | wt | T1014M | wt | wt | wt |
| CO87# | wt | wt | wt | wt | wt | wt | I1030M | wt | wt |
| MX9 | wt | wt | wt | wt | wt | wt | wt | 904-919del | wt |
| CX28 | wt | wt | wt | wt | wt | wt | wt | Y88C | wt |
| HX170 | wt | wt | wt | wt | wt | wt | wt | L325H / LOH | wt |
| HX199 | wt | wt | wt | wt | wt | wt | wt | R74I / F341V | R88Q |
| HX219 | wt | wt | wt | wt | wt | wt | wt | A86P / LOH | wt |
| HX242 | wt | wt | wt | wt | wt | wt | wt | R47S | wt |
| 36 cases | wt | wt | wt | wt | wt | wt | wt | wt | MUT |
| 90 cases | wt | wt | wt | wt | wt | wt | wt | wt | wt |

Amino acid changes or amplifications observed for each gene in 146 colorectal cancers. When two mutations in the same gene in a tumor were observed, the mutations are separated by a slash. "Amp" indicates amplification, "wt" indicates wild-type sequence, "MUT" indicates that the tumors contained a mutation of the PIK3CA gene. "LOH" refers to cases wherein the wild-type allele was lost and only the mutant allele remained, and "del" indicates a deletion of the indicated nucleotide(s). Mutations in double-lined borders are likely to be activating as they either occur in kinase domains or are copy number gains, while mutations in single bold borders are likely to be inactivating either because they are frameshift alterations or because they appear to be biallelic. Tumors with an asterisk indicate those that have a deficiency in DNA mismatch repair, while those with a pound sign indicate those that have mutations in KRAS. Of the 36 tumors with PIK3CA mutations, 27 also had alterations in KRAS.

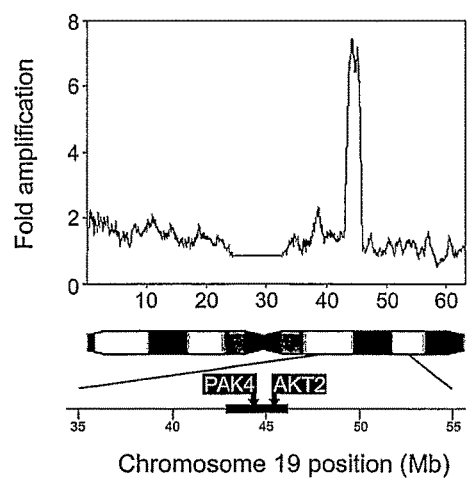
Fig. 6A.
Fig. 6B

PI3K PATHWAY MUTATIONS IN CANCER

This application claims the benefit of provisional application Ser. No. 60/683,738, filed on May 23, 2005, the disclosure of which is expressly incorporated herein.

Funds from the U.S. government were used to make this invention. Therefore, the U.S. government retains certain rights in the invention according to the terms of grants from the National Institutes of Health CA43460 and CA62924.

TECHNICAL FIELD OF THE INVENTION

This invention is related to the area of anti-cancer therapeutics and drug discovery. In particular, it relates to identification of targets suitable for development of specific therapies and to stratification of patients based on status of these targets.

BACKGROUND OF THE INVENTION

Tumors of the colon and rectum are a major health problem: in 2002 alone, a million new cancer cases occurred in the world, resulting in ~590,000 deaths. Half of the population of the United States will develop at least one benign colorectal tumor, and in one-tenth of these, the tumors will eventually become malignant.

Although genetic alterations in tyrosine kinases (TKs) have been firmly implicated in tumorigenesis, only a few serine/threonine kinases (STKs) are known to be mutated in human cancers[1-4]. There is a continuing need in the art to identify genes which are mutated in cancer and which may be good candidates for pharmacological intervention.

SUMMARY OF THE INVENTION

According to one embodiment of the invention a method is provided for screening test substances for use as anti-cancer agents. A test substance is contacted with an activated protein kinase selected from the group consisting of: PDK1, AKT2, and PAK4. The activity of the activated protein kinase is tested. A test substance which inhibits the activity of the activated protein kinase is a potential anti-cancer agent.

Also provided by the present invention is an isolated, activated protein kinase selected from the group consisting of: PDK1, AKT2, and PAK4.

An additional aspect of the invention is a method of categorizing cancers. The sequence of one or more protein kinase family members is determined in a sample of a cancer tissue. The family member is selected from the group consisting of PDK1, AKT2, and PAK4. Alternatively, amplification of AKT2, PAK4, or IRS2 is determined in a sample of a cancer tissue. Either a somatic mutation of said one or more protein kinase family members or amplification of AKT2, PAK4, or IRS2 is detected in the cancer tissue relative to a normal tissue. The cancer tissue is assigned to a set based on the presence of the somatic mutation or the amplification.

An additional aspect of the invention is a method of categorizing cancers. The sequence of one or more protein kinase family members is determined in a sample of a cancer tissue. The family member is selected from the group consisting of MARK3, MYLK2, CDC7, and PD1K1L. A somatic mutation of said one or more protein kinase family members or amplification of MARK3, MYLK2, CDC7, and PD1K1L is detected in the cancer tissue relative to a normal tissue. The cancer tissue is assigned to a set based on the presence of the somatic mutation.

According to one embodiment of the invention a method is provided for screening test substances for use as anti-cancer agents. A test substance is contacted with an activated protein kinase selected from the group consisting of: MARK3, MYLK2, CDC7, and PD1K1L. The activity of the activated protein kinase is tested. A test substance which inhibits the activity of the activated protein kinase is a potential anti-cancer agent.

Also provided by the present invention is an isolated, activated protein kinase selected from the group consisting of: MARK3, MYLK2, CDC7, and PD1K1L.

These and other embodiments which will be apparent to those of skill in the art upon reading the specification provide the art with tools for improving cancer therapy.

BRIEF DESCRIPTION OF THE DRAWINGS

FIG. 2 Serine/threonine kinome genes analyzed.

FIG. 3 Mutations in the serine/threonine kinome in colorectal cancer

FIG. 4 PI3K pathway genes analyzed.

FIG. 5. Mutations of PI3K pathway genes in colorectal cancer. Double-lined border indicates likely activating mutations. Bold-lined border indicates likely inactivating mutations.

FIGS. 6A and 6B. Amplification of AKT2 and PAK4 in colorectal cancers. Amplification of the genomic region containing the AKT2 and PAK4 genes was confirmed in colorectal cancer Co82 by Digital Karyotyping (FIG. 6A) and by FISH on metaphase chromosomes (FIG. 6B) using a probe containing AKT2 and a chromosome 19 control probe.

DETAILED DESCRIPTION OF THE INVENTION

Figure 1:
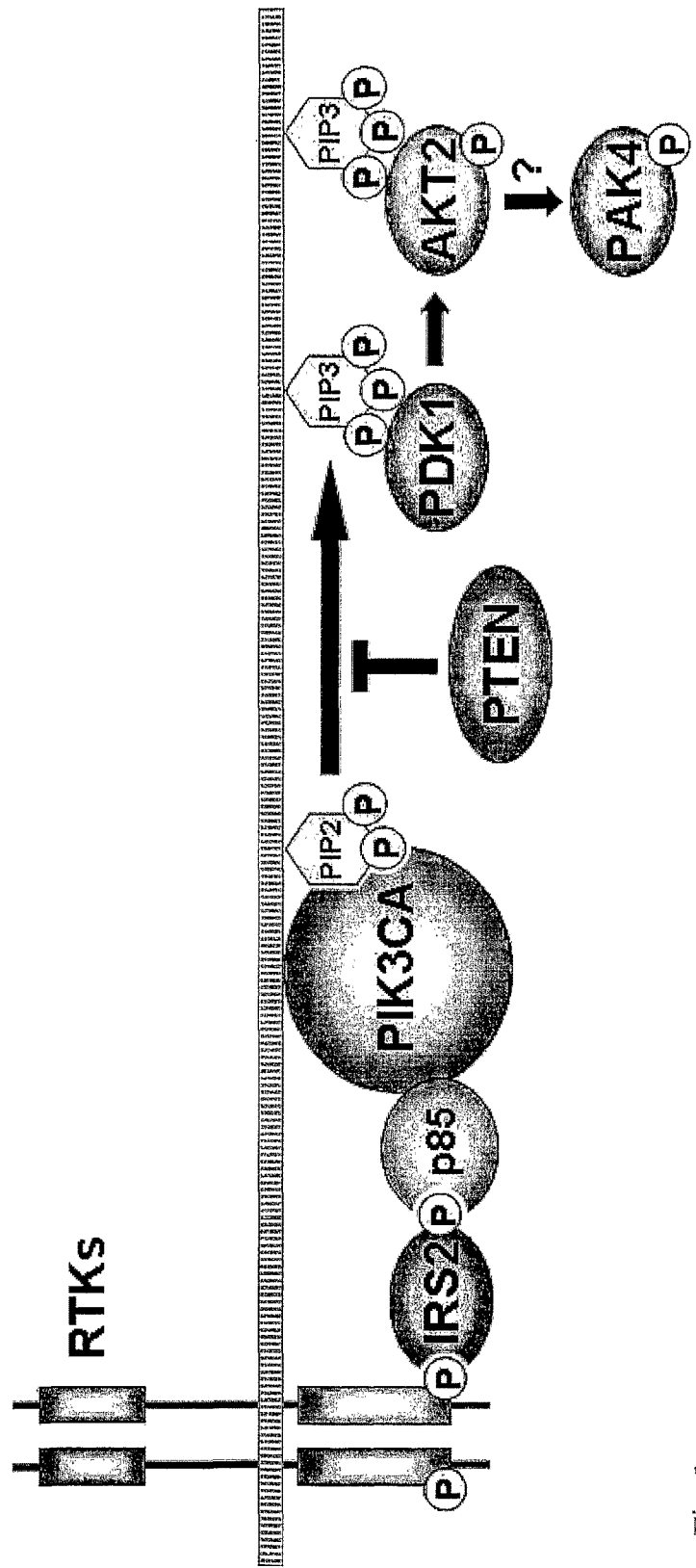
FIG. 1. Mutations of PI3K pathway genes in colorectal cancers. Schematic of the components of the PI3K pathway (reviewed in Ref. 7): Receptor tyrosine kinases (RTKs) recruit IRS adaptor proteins which induce proper assembly of the p85/PIK3CA complex, PIK3CA phosphorylates phosphatidylinositol 4,5 biphosphate (PIP2) to phosphatidylinositol 3,4,5 triphosphate (PIP3), while PTEN normally reverses this process, PDK1 is recruited to the cell surface by PIP3 and directly phosphorylates and activates AKT, and activation of PAK4 is dependent on PI3K signaling, presumably through AKT. Members of the pathway indicated in bold-face type were found to be genetically altered in the colorectal cancers examined in this study.

The inventors have identified therapeutic targets for cancers, including without limitation, colorectal cancer, head and neck cancer, pancreatic cancer, lung cancer, breast cancer, prostate cancer, stomach cancer, and brain cancer. The targets are in two overlapping classes: (a) serine-threonine kinases, and (b) members of the PI3K pathway. Interestingly, the alterations that have been detected in the serine-threonine kinase (STK) members of the PI3K pathway occur in different tumors which do not overlap with tumors containing mutations in PIK3CA or other non-STK members of the PI3K pathway. This suggests that mutations in any of these genes have equivalent tumorigenic effects.

The great majority of the mutations are activating mutations which increase the amount of phosphorylation activity of the kinases. These can be targeted by pharmacological inhibitors to reduce the amount of phosphorylation activity.

Specific inhibitors for specific kinases can be rationally designed or screened for. In order to screen for useful anti-cancer agents, such as anti-colorectal cancer agents, one can contact an activated protein kinase with a test substance. The activated protein kinase can be in a cell, such as a cancer cell, a recombinant host cell, or a cell of a cancer cell line, or it can be isolated from a cell. Typically the activated protein kinase will be one that is found in cancer cells as the result of a somatic mutation. Such activated protein kinases may be PDK1, AKT2, PAK4, MARK3, MYLK2, CDC7, or PD1K1L. Specific activating mutations which may be employed are shown in FIGS. 3 and 5. A test substance which inhibits the activated kinase is a potential anti-cancer agent, and it can be identified as such. It may have particular use as an anti-colorectal cancer agent. Agents which are found to inhibit PDK1, AKT2, and/or PAK4 can be used in particular to treat cancers that have or which have been identified to have PI3KCA mutations. Because these protein kinases are downstream of PI3KCA in the signaling pathway, inhibition of them, even if they are not mutated or activated, may result in reduced signaling from the pathway. Because PI3KCA is one of the most frequently mutated genes in cancers, inhibition of its signaling pathway should be widely effective.

Isolated, activated protein kinases according to the invention are in cell-free preparations. They can be isolated from cancer cells or from recombinant cells. They can be the result of synthetic or semi-synthetic reactions. They can be naturally occurring, activated protein kinases found in actual cancer cells. For purposes of the screening assays, the kinases can be in solution or attached to a solid support, such as a bead, well, column packing material, filter paper, agarose plate, array, etc. Although specific wild-type sequences in databases are referred to in FIGS. 2 and 4, these are of necessity individual sequences of individual humans. Any human sequence can be used for these purposes. Such other human sequences will typically differ very little from the database sequence, perhaps by as little as one, two, three, four, or five amino acid residues. Often such allelic sequences will be conservative changes in which a residue of a certain charge or polarity is replaced with a residue of a similar charge or polarity. Any sequences that are referred to in databases are those sequences as they existed on May 23, 2005.

Samples of cancer tissue from individuals can be tested for the presence of any of the activating mutations of the present invention or amplification of the amplified genes of the present invention. Mutations can be determined by any technique known in the art that is dependent on the sequence of the gene or protein. Direct sequencing of all or part of a gene can be used, for example. Somatic mutations can be determined by comparing a gene or protein sequence in a cancer tissue to that found in a matched tissue of a non-cancer tissue of the same individual. In the absence of a matched tissue, tissues of non-tumor, control individuals can be used. Exemplary mutations are non-synonymous point mutations, splice site alterations, insertions, and deletions. Many techniques are known in the art and any can be used as is convenient. These may include without limitation, allele-specific hybridization, allele-specific amplification, primer extension, mutant-specific antibodies, etc. Amplification can be determined by any technique that permits absolute or relative quantification of a gene sequence. Typically amplification is determined if the sequence is present at least 2-fold, at least 3-fold, at least 5-fold, or at least 10-fold more than in the control. Quantitative PCR, fluorescence in situ hybridization (FISH), and digital karyotyping are techniques that can be used in this regard.

Activating or inactivating mutations can be determined by assaying for kinase (phosphorylation) activity. Any of the multitude of assays known in the art can be used. These include those using radioactive or fluorescent substrates, as well as those in which the substrate is linked to a solid support, tag sequence, or second protein. Typically these assays monitor the amount of phosphorylated protein product. Althernatively, the can monitor the diminution of the amount of one or more substrates. The same assays can be used to test for inhibition of protein kinase activity by test substances. Once an inhibitor is identified in a cell-free or in-cell assay, other assays and tests can be employed to confirm activity and to test for side-effects. Other assays and tests may be in other formats, in other cell types, in whole animals, and in animal models of disease.

If an activating mutation or amplification is detected, then the tissue sample and/or the individual from whom the tissue sample was taken can be assigned to a group or set. The group or set can be used for testing clinical agents for their effects. The group or set can be used to prescribe a treatment regime to the patient. The group or set can be correlated with prognostic information such as life expectancy data or recurrence data. The sets can be tested and/or correlated with drug efficacy data.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Identification of Somatic Mutations in Serine/Threonine Kinases

On the basis of a recent bioinformatics study that identified the protein kinase complement encoded by the human genome[5], we selected 340 serine/threonine kinases for mutational analysis in colorectal cancers. These included 63 A/G/C protein kinases; 74 calcium/calmodulin-dependent protein kinases; 12 casein kinases; 61 CMGC kinases; 47 homologs of yeast sterile 7/11/20 kinases, and 83 other kinases (FIG. 2).

As the catalytic domains of these genes are most likely to harbor mutations that activate the gene product[1], we focused our efforts on the exons containing the kinase domains. These exons were amplified using polymerase chain reaction on template DNA derived from 24 colorectal cancers and directly sequenced (for methods, see Example 4). Any observed change was evaluated in DNA from patient-matched normal tissue to identify somatic (i.e., tumor-specific) mutations. The entire coding regions of those genes found to contain mutations were then further evaluated in a larger panel of 180 colorectal tumors.

Using this approach, a total of 23 changes, including 20 nonsynonymous point mutations, one insertion and one splice site alteration, were identified among the cancers analyzed (FIG. 3). The mutations affected eight different genes: six in mitogen-activated protein kinase kinase 4 (MKK4/JNKK1), six in myosin light chain kinase 2 (MYLK2), three in phosphoinositide dependent protein kinase-1 (PDK1) (of which two mutations affected the same residue in the kinase domain), two in p21-activated kinase 4 (PAK4), two in v-akt murine thymoma viral oncogene homolog 2 kinase (AKT2), and two in MAP/microtubule affinity-regulating kinase 3 (MARKS). One alteration was observed in cell division cycle 7 kinase (CDC7) and another in a hypothetical casein kinase (PDIK1L). Eighteen of the 23 somatic mutations occurred at evolutionarily conserved residues.

EXAMPLE 2

Identification of Somatic Mutations in Serine/Threonine Kinase Members of the PI3K Signaling Pathway Alterations of MKK4/JNKK1 have previously been reported in a variety of various tumor types[6], but none of the other genes had been previously observed to be mutated in colorectal cancers. Interestingly, three of the altered genes, PDK1, AKT2, and PAK4, encoded proteins known to be involved in the phosphatidylinositol-3-kinase (PI3K) signaling pathway (FIG. 1)[7,8], and two of these (AKT2 and PAK4) have been shown to be overexpressed in human cancers[1]. On the basis of these data, we determined whether any of these kinases were altered by amplification, an alternate mechanism for apparent kinase activation. Quantitative PCR analyses of 146 colorectal tumors showed co-amplification of AKT2 and PAK4 on chromosome 19q13.2 in two samples, and these were independently confirmed by Digital Karyotyping[9] and fluorescence in situ hybridization (FISH) (FIG. 6).

EXAMPLE 3

Identification of Somatic Mutations in Non-Serine/Threonine Kinase Members of PI3K Pathway To complement these analyses, we evaluated other non-STK members of the PI3K pathway in the same 146 samples (FIGS. 1 and 4)[7]. These assays revealed one mutation in the insulin related receptor INSRR, one in the v-Erb-B erythroblastic leukemia viral oncogene homolog ERBB4, seven in the phosphatase and tensin homolog PTEN, and three cases of amplification of the insulin receptor substrate IRS2 (FIG. 5). When these alterations were compared to those previously observed in PIK3CA[10], it was found that they were distributed in a striking manner: all but two of the 58 alterations were in different tumors (p=0.02, chi square test). This paucity of overlapping mutations provides strong support for the hypothesis that the mutated genes have equivalent tumorigenic effects and are operating through the same biochemical pathway.

Overall, nearly 40% of colorectal tumors had alterations in one of eight PI3K pathway genes. As most of these genes encode protein kinases, they serve as potential therapeutic targets in tumors containing mutant proteins. In addition, targeting of genes that act downstream in this pathway, such as AKT2 or PDK1, may be effective in targeting the much larger fraction of tumors containing mutations in PIK3CA or PTEN.

EXAMPLE 4

Methods
Selection of STKs and PI3K Pathway Genes for Analysis

All STKs that were members of the following groups identified by Maiming et al.[1] were selected for mutational analysis: the A/G/C protein kinase group (63 genes), the calcium/calmodulin-dependent protein kinase group (74 genes), the casein kinase group (12 genes), the CMGC kinase group (61 genes), the sterile 7/11/20 kinase group (47 genes), and 83 unclassified other protein kinases. Tyrosine kinases and related genes, including members of the TK, TKL, and RGC groups, were not included for analysis as these have been previously examined in colorectal cancers[2]. PI3K pathway genes were identified on the basis of their reported involvement in the PI3K signaling pathway. All STK and PI3K pathway genes analyzed along with Celera and Genbank Accession numbers are listed in FIGS. 2 and 3.

PCR, Sequencing, and Mutational Analysis

Sequences for all annotated exons and adjacent intronic sequences containing the kinase domain of identified STKs and PI3K pathway genes were extracted from the Celera (www.celera.com) or public (http://genome.ucsc.edu/) draft human genome sequences. Primers for PCR amplification and sequencing were designed using the Primer 3 program which is available as an http document at server computer frodo.wi.mit.edu at a file named cgi-bin/primer3/primer3_www.cgi, and were synthesized by MWG (High Point, N.C.) or IDT (Coralville, Iowa). PCR amplification and sequencing were performed on tumor DNA from early passage cell lines or primary tumors as previously described[2] using a 384 capillary automated sequencing apparatus (Spectrumedix, State College, Pa.). Sequence traces were assembled and analyzed to identify potential genomic alterations using the Mutation Surveyor software package (SoftGenetics, State College, Pa.). Sequences of all primers used for PCR amplification and sequencing are available from the authors upon request.

Digital Karyotyping

A Digital karyotyping library of colorectal cancer Co82 was constructed as previously described[3]. Briefly, genomic DNA was isolated using a DNeasy kit (Qiagen, Chatsworth, Calif.). For each sample, 1 μg of genomic DNA was sequentially digested with mapping enzyme SacI (New England Biolabs, Beverly, Mass.), ligated to 20-40 ng of biotinylated linkers (Integrated DNA Technologies, Coralville, Iowa), and digested with the fragmenting enzyme NlaIII (New England Biolabs, Beverly, Mass.). DNA fragments containing biotinylated linkers were isolated by binding to streptavidin-coated magnetic beads (Dynal, Oslo, Norway). Captured DNA fragments were ligated to linkers containing MmeI recognition sites, and tags were released with MmeI (New England Biolabs, Beverly, Mass.). Tags were self-ligated to form ditags which were then further ligated to form concatemers and cloned into pZero (Invitrogen, Carlsbad, Calif.). Clones were sequenced using Big Dye terminators (ABI, Foster City, Calif.) and analyzed using a 384 capillary automated sequencing apparatus (Spectrumedix, State College, Pa.) or with a 96 capillary ABI 3700 instrument at Agencourt Biosciences (Beverly, Mass.). Digital karyotyping sequence files were trimmed using Phred sequence analysis software (CodonCode, Mass.) and 21 bp genomic tags were extracted using the SAGE2000 software package. Tags were matched to the human genome (UCSC human genome assembly, July 2003 freeze) and tag densities were evaluated using the digital karyotyping software package. Genomic densities were calculated as the ratio of experimental tags to the number of virtual tags present in a fixed window. Sliding windows of sizes ranging from 100 to 300 virtual tags were used to identify regions of increased and decreased genomic density. Digital karyotyping protocols and software for extraction and analysis of genomic tags are available as an http document, at server computer www.digitalkaryotyping.org.

FISH

Metaphase chromosomes were analyzed by FISH as previously described[4]. BAC clone CTC-425O23 (located at chr19: 45,387,867-45,566,201 bp) and RP11-21J15 (located at chr19: 49,726,611-49,900,195) were obtained from Bacpac Resources (Children's Hospital Oakland, Calif.) and used as probes for the AKT2 gene and a reference region on chromosome 19, respectively. CTC-425O23 and RP11-21J15 were labeled by nick translation with biotin-dUTP and digoxigenin-dUTP, respectively. To detect biotin-labeled and digoxigenin-labeled signals, slides were first incubated with FITC-avidin (Vector, Burlingame, Calif.) and an anti-digoxigenin mouse antibody (Roche, Indianapolis, Ind.). The slides were subsequently incubated with a biotinylated anti-avidin antibody (Vector, Burlingame, Calif.) and TRITC-conjugated rabbit anti-mouse antibody (Sigma, St. Louis, Mo.), then finally incubated with FITC-avidin and TRITC-conjugated goat anti-rabbit antibody (Sigma). Slides were counterstained with 4',6'-diamidino-2-phenylindole stain (DAPI) (Sigma, Burlingame, Calif.). FISH signals were evaluated with a Nikon fluorescence microscope E800.

Quantitative PCR

Amplification of AKT2, PAK4, and IRS2 genes was determined by quantitative real-time PCR using an iCycler apparatus (Bio-Rad, Hercules, Calif.) as previously described[3,4]. DNA content was normalized to that of Line-1, a repetitive element for which copy numbers per haploid genome are similar among all human cells. PCR primers with the following sequences were used to amplify AKT2, PAK4, and IRS2 respectively: AKT2-F 5'-GGACA-GGGAAGAGACCCTTTTT-3' (SEQ ID NO: 1), AKT2-R 5'-TAACACGAGGATGGGATGTTTG-3(SEQ ID NO: 2)', PAK4-F 5'-TAGGCCATTTGTCCTGGAGTTT-3'(SEQ ID NO: 3), PAK4-R 5'-CTTCTCAACCCACTCGCTTTTT-3' (SEQ ID NO: 4), IRS2-F: 5'-CAAGGAAGACCAAC-CATGGAG-3'(SEQ ID NO: 5) and IRS2-R 5'-AGGAGCA-GAGACACCTGCAAC-3'(SEQ ID NO: 6). PCR reactions for each sample were performed in triplicate and threshold cycle numbers were calculated using iCycler software v2.3 (Bio-Rad Laboratories, Hercules, Calif.).

References for Example 4 Only

1. Manning, G., Whyte, D. B., Martinez, R., Hunter, T. & Sudarsanam, S. The protein kinase complement of the human genome. *Science* 298, 1912-34. (2002).
2. Bardelli, A. et al. Mutational analysis of the tyrosine kinome in colorectal cancers. *Science* 300, 949 (2003).
3. Wang, T. L. et al. Digital karyotyping. *Proc Natl Acad Sci USA* 99, 16156-61 (2002).
4. Wang, T. L. et al. Digital karyotyping identifies thymidylate synthase amplification as a mechanism of resistance to 5-fluorouracil in metastatic colorectal cancer patients. *Proc Natl Acad Sci USA* 101, 3089-94 (2004).
5. Vivanco, I. & Sawyers, C. L. The phosphatidylinositol 3-Kinase AKT pathway in human cancer. *Nat Rev Cancer* 2, 489-501 (2002).
6. Wells, C. M., Abo, A. & Ridley, A. J. PAK4 is activated via PI3K in HGF-stimulated epithelial cells. *J Cell Sci* 115, 3947-56 (2002).
7. Steck, P. A. et al. Identification of a candidate tumour suppressor gene, MMAC1, at chromosome 10q23.3 that is mutated in multiple advanced cancers. *Nat Genet* 15, 356-62 (1997).
8. Li, J. et al. PTEN, a putative protein tyrosine phosphatase gene mutated in human brain, breast, and prostate cancer. *Science* 275, 1943-7 (1997).
9. Samuels, Y. et al. High frequency of mutations of the PIK3CA gene in human cancers. *Science* 304, 554 (2004).
10. Philp, A. J. et al. The phosphatidylinositol 3'-kinase p85alpha gene is an oncogene in human ovarian and colon tumors. *Cancer Res* 61, 7426-9 (2001).
11. Zhang, B. & Roth, R. A. The insulin receptor-related receptor. Tissue expression, ligand binding specificity, and signaling capabilities. *J Biol Chem* 267, 18320-8 (1992).
12. Cohen, B. D., Green, J. M., Foy, L. & Fell, H. P. HER4-mediated biological and biochemical properties in NIH 3T3 cells. Evidence for HER1-HER4 heterodimers. *J Biol Chem* 271, 4813-8 (1996).

REFERENCES

The disclosure of each reference cited is expressly incorporated herein.

1. Blume-Jensen, P. & Hunter, T. Oncogenic kinase signaling. *Nature* 411, 355-65. (2001).
2. Bardelli, A. et al. Mutational analysis of the tyrosine kinome in colorectal cancers. *Science* 300, 949 (2003).
3. Davies, H. et al. Mutations of the BRAF gene in human cancer. *Nature* 417, 949-54 (2002).
4. Futreal, P. A. et al. A census of human cancer genes. *Nat Rev Cancer* 4, 177-83 (2004).
5. Manning, G., Whyte, D. B., Martinez, R., Hunter, T. & Sudarsanam, S. The protein kinase complement of the human genome. *Science* 298, 1912-34. (2002).
6. Teng, D. H. et al. Human mitogen-activated protein kinase kinase 4 as a candidate tumor suppressor. *Cancer Res* 57, 4177-82 (1997).
7. Vivanco, I. & Sawyers, C. L. The phosphatidylinositol 3-Kinase AKT pathway in human cancer. *Nat Rev Cancer* 2, 489-501 (2002).
8. Wells, C. M., Abo, A. & Ridley, A. J. PAK4 is activated via PI3K in HGF-stimulated epithelial cells. *J Cell Sci* 115, 3947-56 (2002).
9. Wang, T. L. et al. Digital karyotyping. *Proc Natl Acad Sci USA* 99, 16156-61 (2002).
10. Samuels, Y. et al. High frequency of mutations of the PIK3CA gene in human cancers. *Science* 304, 554 (2004).

We claim:

1. A method comprising:
   performing an assay on a sample of a cancer tissue of a human that has:
   a methionine codon at codon 354 or a glutamine codon at codon 527 of protein kinase family member gene PDK1, or
   a glycine codon at codon 302 or a histidine codon at codon 371 of protein kinase family member gene AKT2,
   wherein the assay tests codon 354 or codon 527 of the PDK1 gene, residue 354 or residue 527 of the PDK1 protein kinase, codon 302 or codon 371 of the AKT2 gene, or residue 302 or 371 of AKT2 protein kinase and detects said residue.

2. The method of claim 1 wherein the cancer tissue is a colorectal cancer tissue.

3. The method of claim 1 wherein the assay tests protein kinase family member PDK1.

4. The method of claim 1 wherein the assay tests protein kinase family member AKT2.

5. The method of claim 1 further comprising the step of placing the human in an arm of a clinical trial.

6. The method of claim 1 wherein the assay is selected from the group consisting of: nucleotide sequencing, allele specific hybridization, allele specific amplification, primer extension, and mutant specific antibody binding.

7. A method comprising:
   testing a sample of a colorectal cancer tissue of a human that contains an amplified AKT2 gene for amount of AKT2 gene in the colorectal cancer tissue relative to amount of a genomic control in said colorectal cancer tissue.

8. The method of claim 7 wherein amplification of at least 5-fold is determined.

9. The method of claim 7 further comprising the step of placing the human in an arm of a clinical trial.

10. The method of claim 7 wherein the genomic control is a chromosome 19 reference region.

11. The method of claim 7 wherein the testing employs an assay selected from the group consisting of: quantitative polymerase chain reaction, fluorescence in situ hybridization, digital karyotyping, and a kinase phosphorylation assay.

12. A method comprising:
hybridizing nucleic acids of a sample of a cancer tissue of
a human that has
a methionine codon at codon 354 or a glutamine codon at codon 527 of protein kinase family member gene PDK1, or
a glycine codon at codon 302 or a histidine codon at codon 371 of protein kinase family member gene AKT2,
with an oligonucleotide that hybridizes to said codon in the protein kinase family member gene; and
detecting hybridization, or extending the oligonucleotide, or amplifying by extending the oligonucleotide.

13. A method comprising:
contacting proteins in a sample of a cancer tissue of a human that has
a methionine residue at residue 354 or a glutamine residue at residue 527 of protein kinase family member PDK1, or
a glycine residue at residue 302 or a histidine residue at residue 371 of protein kinase family member AKT2,
with an antibody that is specific for said residue in the protein kinase family member, and
detecting binding of the antibody to proteins in the sample.

* * * * *

UNITED STATES PATENT AND TRADEMARK OFFICE
CERTIFICATE OF CORRECTION

Page 1 of 1

PATENT NO.         : 9,580,750 B2
APPLICATION NO.    : 11/920860
DATED              : February 28, 2017
INVENTOR(S)        : Donald William Parsons et al.

It is certified that error appears in the above-identified patent and that said Letters Patent is hereby corrected as shown below:

In the Specification

Column 1 Line 6 replace with the following:
STATEMENT OF GOVERNMENTAL INTEREST
This invention was made with government support under grant number CA043460, CA062924, awarded by the National Institutes of Health. The government has certain rights in the invention.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 6

<210> SEQ ID NO 1
<211> LENGTH: 22
<212> TYPE: DNA
<213> ORGANISM: Homo sapiens

<400> SEQUENCE: 1
ggacagggaa gagacccttt tt          22

```
<210> SEQ ID NO 2
<211> LENGTH: 22
<212> TYPE: DNA
<213> ORGANISM: Homo sapiens

<400> SEQUENCE: 2
taacacgagg atgggatgtt tg                                              22

<210> SEQ ID NO 3
<211> LENGTH: 22
<212> TYPE: DNA
<213> ORGANISM: Homo sapiens

<400> SEQUENCE: 3
taggccattt gtcctggagt tt                                              22

<210> SEQ ID NO 4
<211> LENGTH: 22
<212> TYPE: DNA
<213> ORGANISM: Homo sapiens

<400> SEQUENCE: 4
cttctcaacc cactcgcttt tt                                              22

<210> SEQ ID NO 5
<211> LENGTH: 21
<212> TYPE: DNA
<213> ORGANISM: Homo sapiens

<400> SEQUENCE: 5
caaggaagac caaccatgga g                                               21

<210> SEQ ID NO 6
<211> LENGTH: 21
<212> TYPE: DNA
<213> ORGANISM: Homo sapiens

<400> SEQUENCE: 6
aggagcagag acacctgcaa c                                               21
```